United States Patent [19]

Siuciak

[11] Patent Number: 5,599,560

[45] Date of Patent: Feb. 4, 1997

[54] METHOD OF TREATING DEPRESSION USING NEUROTROPHINS

[75] Inventor: Judith Siuciak, Tarrytown, N.Y.

[73] Assignee: Regeneron Pharmaceuticals, Inc., Tarrytown, N.Y.

[21] Appl. No.: 337,321

[22] Filed: Nov. 10, 1994

Related U.S. Application Data

[63] Continuation of Ser. No. 47,819, Apr. 15, 1993, abandoned.

[51] Int. Cl.$^6$ .......................... A61K 38/18; A61K 35/30; A01N 37/18

[52] U.S. Cl. ................................ 424/570; 514/2; 514/12; 530/399

[58] Field of Search ..................................... 514/2, 21, 12; 424/570

[56] References Cited

U.S. PATENT DOCUMENTS

| | | | |
|---|---|---|---|
| 5,169,764 | 12/1992 | Shooter et al. | 435/69.7 |
| 5,229,500 | 7/1993 | Barde | 530/399 |
| 5,364,769 | 11/1994 | Rosenthal | 435/69.1 |
| 5,488,099 | 1/1996 | Persson | 530/399 |

OTHER PUBLICATIONS

Danysz, W., et al., "Screening for new antidepressant compounds", Behavioural Models in Psychopharmacology, Paul Wilner, Ed., Cambridge University Press, Port Chester, NY 10573 (1991), Chapter 6, pp. 126–156.

Deakin, J. F. W., "The clinical relevance of animal models of depression", Behavioural Models In Psychopharmacology, Paul Wilner, Ed., Cambridge University Press, Port Chester, NY 10573 (1991), Chapter 7, pp. 157–174.

Lucki, Irwin, "Behavioural Studies of Serotonin Receptor Agonists as Antidepressant Drugs", J. Clin. Psychiatry 52-12 (suppl)., Dec. 1991, pp. 24–31.

Porsolt, R. D., et al., "Behavioural Despair In Rats: A New Model Sensitive to Antidepressant Treatments", European Journal of Phamacology, 47 (1978), pp. 379–391.

Porsolt, R. D., et al., "Immobility Induced By Forced Swimming In Rats: Effects of Agents Which Modify Central Catecholamine and Serotonin Activity", European Journal of Pharmacology, 57 (1979), pp. 201–210.

Wilner, P., "Animal models of depression", Behavioural Model In Psychopharmacology, Paul Wilner, Ed., Cambridge University Press, Port Chester, NY 10573 (1991), Chapter 5, pp. 91–119.

Lamballe, F., et al. Cell 66:967–979 Sep. 6 1991.

Gregoriadis, G. and Florence, A. T. Trends Biotech. 11:440–442 Nov. 1993.

Squinto, S. P., et al. Cell 65:885–893 May 31 1991.

Klein, R., et al. Cell 66:395–403 Aug. 26 1991.

Klein, R., et al. Neuron 8:947–956, May 1992.

Soppet, D., et al. Cell 65:895–903, May 31 1991.

Snyder, S. H. Nature 350:195–196, Mar. 21 1991.

Knusel, B., et al. Proc. Natl. Acad. Sci. U.S.A. 88:961–965, Feb. 1991.

Hyman, C., et al. Nature 350:230–232, Mar. 21 1991.

Kandel, E. R., et al. "Principles of Neural Science", Elsevier Science Publishing, 1991.

Fingl, E. and Woodbury, D. M. in "The Pharmacological Basis of Therapeutics" (L. S. Goodman and A. Gilman eds.) Macmillan Publishing Co., Inc. pp. 1–46, 1975.

Ip, N.Y., et al. Proc. Natl. Acad. Sci. U.S.A. 89:3060–3064, Apr. 1992.

*Primary Examiner*—Lila Feisee
*Assistant Examiner*—John Lucas
*Attorney, Agent, or Firm*—Gail Kempler

[57] ABSTRACT

Infusion of neurotrophins, preferably brain-derived neurotrophic factor, are shown to be effective agents for use in the alleviation of symptoms of depression, as demonstrated by reduction of "despair" in the animal forced swim test. Alterations in serotonin levels brought about by neurotrophins suggest use of these factors for the treatment of other disorders caused by defects in serotonin activity.

3 Claims, 2 Drawing Sheets

METHOD OF TREATING DEPRESSION USING NEUROTROPHINS

This is a continuation of application Ser. No. 08/047,819 filed Apr. 15, 1993, now abandoned.

INTRODUCTION

The present invention relates to a method of treating or alleviating the symptoms of depression. It is based, in part, on the discovery that midbrain infusions of specific neurotrophic factors results in a reduction in depression, as measured by identifiable behavior in animal systems used to identify therapeutically effective anti-depressive agents.

BACKGROUND OF THE INVENTION

It has been estimated that approximately 4% of the people in the world suffer from depression which is not caused by any underlying neurological disease. Depression effects people in all walks of society, from the very young to the very old. It often occurs without the presence of a precipitating event, and is frequently unresponsive to psychotherapy or environmental changes.

The cluster of symptoms associated with depression suggests that it is caused by a defect which affects the regulation of neurotransmitters. Neurotransmitters are substances that are synthesized and released synaptically by one neuron and which effect a postsynaptic cell through a specific receptor. The major small molecule transmitter substances include acetylcholine, the biogenic amines such as dopamine, norepinephrine, serotonin and histamine, as well as amino acids such as glutamate. Neurons also communicate with other neurons or target cells through the neuroactive peptides, which include somatostatin and β-endorphin. Neuronal cells often produce a combination of small molecule transmitters and neuroactive peptides at their synapses.

Present theory postulates that a deficiency in the neurotransmitters serotonin and/or norepinephrine, or both, results in the symptoms of depression. Norepinephrine is synthesized from tyrosine through the enzymes tyrosine hydroxylase, which converts tyrosine to L-DOPA, which in turn is acted on by a decarboxylase to give dopamine, which is then acted on by dopamine β-hydroxylase, converting dopamine to norepinephrine. Serotonin is synthesized from tryptophan through the action of the enzymes tryptophan hydroxylase, which oxidizes tryptophan to 5 hydroxytryptophan (5-OH-tryptophan), and the enzyme 5-OH-tryptophan decarboxylase, which converts 5-OH-tryptophan to serotonin (5 hydroxytryptamine; 5HT). Once synthesized by a neuronal cell, serotonin and norepinephrine are stored within the cell in vesicles.

In the central nervous system (CNS), norepinephrine-containing nerve cell bodies are present in the locus ceruleus (among other areas) which projects throughout the cortex, cerebellum and spinal cord. In the peripheral nervous system, the postganglionic neurons of the sympathetic nervous system use norepinephrine as a neurotransmitter.

Serotonin containing cell bodies are present in the midline raphe nuclei, which projects throughout the brain and spinal cord. Multiple families of serotonin receptors exist in the CNS, including the 5-HT$_1$ (subtypes 5-HT$_{1A}$, 5-HT$_{1B}$ and 5-HT$_{1C}$, and 5-HT$_{1D}$) as well as 5-HT$_2$, 5-HT$_3$ and 5-HT$_4$ families of receptors. Each 5-HT receptor is associated with an individual pharmacology for agonists and antagonists. (Frazer A., et al. Annual Rev. Pharmacol. Toxicol. 1990; 30: 307–348; Bockaert J., et al. Mol. Pharmacol 1990; 37: 408–411). For example, 5-HT$_{1A}$ agonists are potent antidepressants.

When norepinephrine or serotonin containing neurons are stimulated, these transmitters are released to act transiently on effector cells or organs, to alter the conductance of ions through channels of the postsynaptic membrane, or to alter the biochemical activity within the cell. Removal of neurotransmitters from the synaptic cleft may entail breakdown by cytoplasmic enzymes or reuptake into vesicles in presynaptic neurons.

The theory that depression is associated with a regulatory imbalance involving the biogenic amines serotonin and norephinephrin originated with studies involving reserpine. This compound, which can be used to induce depression, interferes with the granular storage of biogenic amines in presynaptic neurons, thus causing their release and eventual depletion.

Two therapies are generally used to treat depression, which may have a mode of action which alters, at least temporarily, regulatory imbalances in the biogenic amines. The first is electroconvulsive therapy (ECT), which, in effect, causes the induction of a generalized seizure. ECT has been found to cause an improvement in approximately 90% of patients on which it is used.

Antidepressant drugs include the monoamine oxidase inhibitors and the tricyclic compounds, both of which are effective in about 70% of the cases in which they are used. The monoamine oxidase inhibitors prevent the degradation of cytoplasmic serotonin and norepinephrine. The tricyclic compounds block the active reuptake of serotonin and norepinephrine by neurons, thus permitting these transmitters a longer time to act in the synaptic cleft. In addition, serotonin precursors such as tryptophan and 5 HT act as antidepressants.

In addition to a serotonergic mechanism, there is some evidence that drugs acting via a dopaminergic mechanism may have antidepressant activity. Tricyclic antidepressants appear to affect the dopaminergic system at the presynaptic level by enhancing the release of dopamine. Chiodo, L. A. et al. 1980; Eur. J. Pharmacol 63:203–204.

Thus, although the specific cause of depression has not been fully elucidated, the biogenic amines appear to play a significant role in the process. It appears, therefore, that agents that alter the intracellular and extracellular levels of these compounds in the brain would be expected to have some effect on depression.

One group of compounds that have recently been found to be active in altering serotonin turnover in the brain are the neurotrophins. The neurotrophin family includes brain-derived neurotrophic factor (BDNF), neurotrophin-3 (NT-3) and neurotrophin-4 (NT-4), all of which have recently been molecularly cloned and shown to be members of the nerve growth factor (NGF) family by virtue of their sequence homology [Leibrock, et al., Nature 341: 149–152, (1989); Hohn, et al., Nature, 344: 339–341, (1990); Maisonpierre, et al., Science, 247: 1446–1451, (1990a); Rosenthal, et al., Neuron, 4: 767–773, (1990); Ernfors, et al., Proc. Natl. Acad. Sci., U.S.A., 87: 5454–5458 (1990); Jones and Reichardt,, Proc. Natl. Acad. Sci. U.S.A. 87: 8060–8064 (1990); Hallbook, et al., Neuron 6: 845–858, (1991); Ip, et al., Proc. Natl. Acad. Sci., U.S.A., 89: 3060–3064 (1992)]. This family of proteins plays an important role in both the developing and the adult vertebrate nervous system, where these proteins support neuronal survival.

Studies involving the in vivo actions of the neurotrophins, in particular the neurotrophin BDNF, have confirmed their actions in maintaining the survival and regulating the function or phenotype of various neuronal cells. Chronic intraseptal infusions of BDNF can prevent most of the axotomy-induced loss of cholinergic neuron staining in the medial septum [Morse et al, in press]. In otherwise intact rats, chronic infusions of BDNF above the substantia nigra elevate dopamine metabolism, as determined by increases in HVA concentrations in the ipsilateral caudate-putamen and even larger elevations in the DOPAC/dopamine and HVA/dopamine ratios [Altar, et al., In Vivo, Proc. Natl. Acad. Sci., (USA) (in press)]. A recent report described the in vitro survival effect of NT-3 and NT-4 (but not NGF) on locus ceruleus neurons (Friedman, et al. Exp. Neurol 119: 72–78 (1993).

There is also ample evidence of the presence of neurotrophin receptors in areas of the brain that are associated with depression. For example, high affinity binding sites for [125I]NT-3 are found within the medial substantia nigra and ventral tegmental area, nucleus accumbens, caudate-putamen, and raphe nucleus, and the binding to these sites is potently displaced by BDNF [Altar, et al., Am. Acad. Neurol. San Diego, Calif., (1992)]. BDNF mRNA is also present in these areas and appears to overlap with TOH-positive cells [Gall, et al., (1992)]. Intrastriatal injections of [125I]-labeled NT-3 or BDNF result in retrograde transport and accumulation of radioactivity within TOH-positive cells in these same regions, and intrastriatally injected [125I]-labelled BDNF or infused cold BDNF is transported to the median raphe area of the midbrain, which includes a large population of serotonergic neurons [Wiegand, et al., Soc. Neurosci. AB., 17: 1121, (1991)]. In brain sections, NT-4 binding has been found to be widely distributed throughout the brain including the cortex, striatum, hippocampus, cerebellum, olfactory bulbs, periaqueductal gray, and raphe nuclei.

Based on the in vitro activities as well as in vivo binding data, it is expected that the actions of BDNF, NT-3 and NT-4 will extend to brain regions containing or innervated by these neurons.

As described in copending Ser. No. 07/944,823 filed on Sep. 14, 1992, which in incorporated by reference herein, several members of the neurotrophin family have analgesic properties that may be due to their ability to alter serotonin neurotransmission within the brain or spinal cord. Infusions of BDNF and NT-3 in the area of the raphe nucleus resulted in elevated levels of serotonin, which may subsequently effect release of enkephalin or other naturally occurring opioids, thus causing the analgesia observed following their infusion. The effect of this alteration in serotonin metabolism on psychiatric disorders has not, to date, been reported.

SUMMARY OF THE INVENTION

The object of the present invention is to provide a method for treating depression in humans.

Another object of the present invention is to provide a novel class of biologics useful for the treatment of depression.

Yet another object of the invention is provide a method of treating diseases or disorders that are caused by defects in serotonin metabolism.

These and other objects are achieved by the present invention, in which it is shown that neurotrophic factors, specifically members of the neurotrophin family, can be used to treat depression, as well as other serotonin-linked diseases or disorders, in mammals.

DETAILED DESCRIPTION OF THE INVENTION

Figure 1:
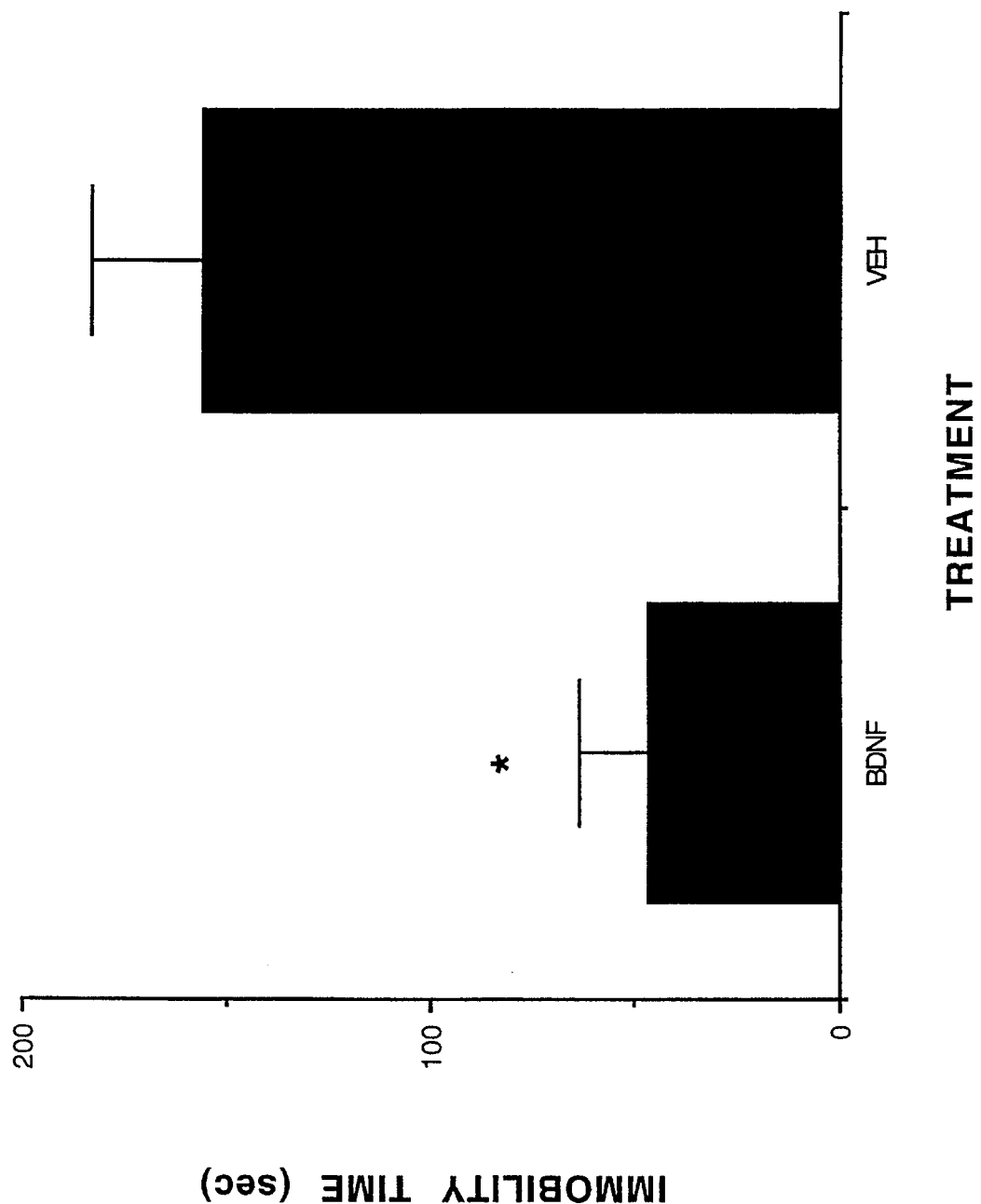
FIG. 1 Duration of immobility in the forced swim test in rats receiving midbrain infusions of PBS vehicle or BDNF (24 ug/day). The values shown are mean+SEM for 4–5 rats/group. Students t test $p<0.01$.

The present invention provides a novel method for treating depression which involves the use of neurotrophic factors, specifically the NGF family of neurotrophins. Although not wishing to be bound by theory, these neurotrophins are believed to be active for the treatment of depression based on their ability to alter serotonin turnover in the brain. As described above, the present theory of depression has linked depression to reduced serotonin levels, possibly caused by either enhanced breakdown of serotonin or decreased serotonin uptake by receptors on postsynaptic cells. Applicants had previously demonstrated that the neurotrophins BDNF and NT-3 bring about enhanced serotonin levels in the brain. As described herein, animal models used to predict the antidepressant activity of test agents indicate that neurotrophins that alter serotonin levels appear to have such activity.

The search for animal tests that can be used for the routine screening of drugs useful for the treatment of depression has resulted in very few tests that can be used reliably. In fact, most antidepressant drugs have been discovered using pharmacological test methods developed using drugs with known anti-depressant activity. Such tests, therefore, would not be expected to be useful to identify agents that have a different mode of action than those currently used.

One animal model that has proven to be promising with regard to predicting antidepressant activity of test compounds is the "forced swim test". (Porsolt, R. D., 1978, Eur. J. Pharmacology, 47, 379–391). According to this model, rats are forced to swim in a restricted space from which they cannot escape. Such rats eventually cease attempting to escape and become immobile, save those movements necessary to keep their heads above water. It has been suggested that this immobile state reflects a state of despair. According to the model, agents that reduce this state of despair decrease the immobility of the rats. Thus, therapeutic agents effective for treating depression can be identified as those that increase the mobility of the rats.

Although it has been suggested (Porsolt, et al. Eur. J. Pharmacol. 57(1979) 201–210) that the forced swim model used herein to confirm the antidepressant activity of neurotrophic factors may not be useful to identify those compounds that act primarily on 5 HT, the same authors report that amitriptyline, which is believed to be primarily serotinergic, was the most active of the tricyclic compounds tested for reduced immobility in the swim test. Furthermore, the serotonin uptake blocker imipramine was also very active in reduced immobilization in the forced swim test.

Based on the activity of neurotrophic factors, especially those members of the neurotrophin family, in these animal models, applicants have discovered that the neurotrophins are useful for the treatment of depression. The concentration of the active ingredient used in the formulation will depend upon the effective dose required and the mode of administration used. The dose used should be a therapeutically effective dose; i.e. a sufficient dose to deliver efficacious concentrations of active ingredient to the target areas.

In a preferred embodiment of the invention, BDNF and/or NT-3 are delivered into the midbrain tegmentum, near the periaqueductal gray and the dorsal raphe, areas of the brain which contain an abundance of serotonergic neurons.

In a preferred embodiment, the neurotrophin BDNF is used to reduce depression. As described in Example 1, infusions of this factor resulted in a significant reduction in immobility in the forced swim test, which, as is further described in Example 1, was not attributable to increased locomotor activity.

Definitive studies have indicated that BDNF primarily uses the trkB receptor [Squinto, et al., Cell 65: 885–893 (1991);], which is found in abundance in the midbrain tegmentum, the periaqueductal gray and the dorsal raphe. The neurotrophin NT-4 also primarily uses the trkB receptor [Ip, et al., Proc. Natl. Acad. Sci., U.S.A., 89: 3060–3064 (1992)] and therefore would be expected to produce similar results.

In addition, previous studies have also shown abundant trkC receptor (which preferentially binds NT-3 [Lamballe, et al., Cell 66: 967–979 (1991)] in the area of infusion, and such studies have also indicated that NT-3 causes an increase in serotonin levels when infused into the midbrain tegmentum. Accordingly, NT-3, as well as other factors that bind trkC, would be expected to have activity as antidepressants.

In addition to the native neurotrophins, it is further contemplated that chimeras, or peptides or fragments derived from the neurotrophins, or any small molecules which act as agonists to the trkB or trkC receptor, will be useful to practice the present invention, and may provide the possibility of improved delivery.

For example, neurotrophins useful for practicing the present invention may be obtained by expressing the genes, the sequences of which are described in the literature (see BACKGROUND OF THE INVENTION). Each cloned gene may then be expressed in a prokaryotic or eukaryotic expression system. Any of a number of protocols available to one skilled in the art may be utilized to clone and sequence the neurotrophins. The recombinant neurotrophin gene may be expressed and purified utilizing any number of methods. In a preferred, nonlimiting embodiment of the invention, each factor may be prepared from bacterial cells or eukaryotic cells that express recombinant factor. The gene encoding the factor may be subcloned into a bacterial expression vector, such as for example, but not by way of limitation, pCP110.

The recombinant factors may be purified by any technique which allows for the subsequent formation of a stable, biologically active protein. For example, and not by way of limitation, the factors may be recovered from cells as inclusion bodies, followed by quantitative extraction in 8M guanadinium chloride and dialysis. In order to further purify the factors, conventional ion exchange chromatography, hydrophobic interaction chromatography, reverse phase chromatography or gel filtration may be used.

The active ingredient, which may comprise one purified neurotrophin, or a hybrid, peptide fragment or mutant thereof, a combination of several neurotrophins, or a combination of neurotrophin and other known antidepressant, should be formulated in a suitable pharmaceutical carrier for administration in vivo by any appropriate route including, but not limited to injection (e.g., intravenous, intraperitoneal, intraparenchymal, intracranial, intramuscular, subcutaneous, endoneural, perineural, intraspinal, intracerebroventricular, intrathecal etc.), by absorption through epithelial or mucocutaneous linings (e.g., oral mucosa, rectal and intestinal mucosa, etc.); or by a sustained release implant, including a cellular or tissue implant, or by implantation of naturally occurring or engineered cells capable of producing therapeutic levels of the factors, or by introduction of neurotrophic-factor encoding genetic material directly into the brain.

Using recombinant DNA techniques, the present invention provides for the production of target cells which are engineered to express therapeutic levels of neurotrophic factors. The factor-encoding gene may be inserted into target cells using any method known in the art, including but not limited to transfection, electroporation, calcium phosphate/DEAE dextran methods, and cell gun. (see, for example, Freese, et al. (1991) Nucleic Acids Research 19: 7219–7223.). Cells expressing the appropriate factor may be delivered and/or implanted to therapeutically treat patients suffering from depression or other related disorders.

Alternatively, using known techniques of gene therapy, target cells in vivo may be transfected with the appropriate gene using, for example, delivery by viral vector, liposomes, or other methods known to those in the art [see, for example, Debs, R. (1992) Proc. Natl. Acad. Science (USA) 89: 11277–11281; Legendre, et al. (1992), Pharmaceutical Research 9:1235–1242].

Alternatively, infusions of neurotrophins may be made into the nucleus accumbens or along the projections of serotonin neurons, especially adjacent to the raphe nucleus.

Depending upon the mode of administration, the active ingredient may be formulated in a liquid carrier such as saline, incorporated into liposomes, microcapsules, polymer or wax-based and controlled release preparations, or formulated into tablet, pill or capsule forms.

The mechanism of action of the factors described herein on depression is not known. It has been postulated, however, that the mechanism involves alterations in serotonin metabolism. Accordingly, the present invention further contemplates the use of such neurotrophins to treat other disorders, such as disorders effecting mood, sleep, sexual activity, appetite, circadian and seasonal rhythms, neuroendocrine function, body temperature, motor activity and cognitive function, associated with serotonin [Meltzer, H Y. 1987, Psychopharmacology: 513–526]. For example, aggressive behavior is reduced in animals by drugs that enhance serotonergic function [Pucilowski, O., et al. Behav. Brain Res. 1983,9: 33–48; Miczek K. A., et al. Behavioral Pharmacology of 5-HT;1989: 117–144]. Accordingly, the neurotrophins may prove useful in the treatment of violent behavior in psychiatric patients. Serotonin uptake inhibitors are also clinically useful for a variety of disorders including bulimia, alcoholism, obsessive compulsive disorders, depression, panic disorders and obesity. Serotonin uptake inhibitors have also been shown to enhance memory processing in mice.

Example 1

Antidepressant activity of BDNF in an Animal Model

1.1 Materials and Methods

1.11 Production and Purity of BDNF

Recombinant human BDNF (Barde et al, 1987 EMBO J. 1: 549–553.) was produced by expression of the gene, complete with its precursor sequence, in Chinese hamster ovary (CHO) cells grown in serum free media [see PCT/US92/04228 entitled "Methods of Treatment of Motorneuron Diseases Using Members of The BDNF/NT-3 Gene Family]. BDNF was monitored for biological activity using dissociated lumber dorsal root ganglia (DRG) cells from E8 chicken embryos maintained 2 days in vitro (Lindsay and Peters, 1984, Neurosci. 12: 45–51.). BDNF mediated survival of 30% subpopulations of DRG neurons with $EC_{50}$ values of approximately 0.01 ng/ml.

1.12 Formulation Stability, and Delivery of BDNF

BDNF was diluted in PBS to 1.0 mg/ml (BDNF) and loaded into Alzet 2002 osmotic pumps (Alza Corp., Palo Alto, Calif.; flow rate 0.5 µl/hr). Each pump was connected to 11.2 cm of vinyl tubing (Bolab Products, Lake Havasu City, Ariz.) filled with the same solution contained in the pumps, immersed in a glass vial that contained PBS and maintained at 37° C. for 2 weeks. The effluent was collected into siliconized 1.5 ml polypropylene tubes that contained 400 µl PBS. The collection tubes were replaced with new tubes every 4 days, and the aliquots were measured for biological activity using the dorsal root ganglia outgrowth assay. BDNF retained full biological activity over the 14 days compared to the activity obtained with the same material stored at 2° C.

1.13 Animal Surgery

Male Sprague-Dawley rats (200–240 g; n=6–8/group) were housed and treated in compliance with AALAC guidelines. One day prior to surgery, the flow moderators of the osmotic pumps were fitted with a 2 cm piece of silated PE50 tubing (Micro-Renathane, Braintree Scientific, Braintree, Mass.) and a 28G osmotic pump connector cannula (Plastics One, Inc., Roanoke, Va.) that was 6.8 mm long. The pumps and flow moderators were filled with vehicle (sterile PBS) or BDNF (1 mg/ml to deliver 12 µg each day). All tubing joints were sealed with cyanoacrylate adhesive (Wonder Bond Plus, Borden, Inc., Columbus, Ohio) and the flow moderator was sealed to the pump with melted dental wax. Each rat was anesthetized with an i.p. injection of chloropent (149 mg/kg chlorohydrate and 30.8 mg/kg sodium pentobarbital) and mounted in a small animal stereotaxic apparatus (Kopf, Tijunga, Calif.). A 2 cm long incision was made on the scalp, through which the osmotic pump was inserted and subcutaneously implanted between the shoulder blades. A 1 mm diameter hole was drilled in the calvarium 7.6 mm posterior to bregma, 1 mm lateral to the saggital suture. The cannula was inserted through the skull hole, attached to the skull with cyanoacrylate adhesive, and the scalp incision was closed with wound clips. Verification of cannula placement took place at the time of sacrifice. Animals with incorrect cannula placements were removed from the study and the data was not used for statistical analysis.

1.14 Forced Swim Test

The forced swim test originally described by Porsolt [Eur. J. Pharmacology, 47, 379–391(1978)] is a standard test used to screen compounds for anti-depressant like activity. Swim sessions are conducted by placing rats in plastic containers containing 16 inches of water 23°–25° C., an amount deep enough so that a rat cannot touch the bottom with its hindlimbs or tail, nor can it escape. Two swim sessions are conducted, an initial 15 minute pretest one day prior to surgery and a second 5 minute test on Day 6 after infusion into the midbrain is begun. Each rat's 5 minute test sessions was videotaped for scoring later. The amount of time the animal spends active (swimming, exploring or trying to escape) and the time the rat is immobile (not struggling and making only those movements necessary to keep its head above water) is measured. Drugs with anti-depressant like activity decrease the immobility time.

1.15 Locomotor Activity

Following surgery, rotational behavior was measured with an automated rotational monitor (Rota-Count 8, Columbus Instruments, Columbus, Ohio) with or without the administration d-amphetamine sulfate (3.3 mg free base/kg i.p.) Rats were fitted with a cloth harness and placed in an individual cylindrical transparent plexiglass cage (12 inch diam×16 inch h). The harness was attached to a rotational sensor on the cage lid via a stainless steel cabled tether. Partial (60 degree) rotations were recorded for both clockwise (ipsiversive to the infused hemisphere) and counter-clockwise (contraversive to the infused hemisphere) directions for 80 minutes.

1.16 Neurochemical Measurements

All reagents were obtained from Sigma Chemical Co. (St. Louis, Mo.) unless indicated. At 14 days after the surgery, the animals were sacrificed and the brains removed. The hippocampus and nucleus accumbens were dissected and the samples stored frozen until assay at which time they were homogenized in 10 volumes of 0.32M sucrose. A 45 µl aliquot for indoleamine determinations was added to 5 µl of a 4 N perchlorate, 1 mM ascorbate, 3 µg/ml dihydroxybenzylamine (DHBA) internal standard solution. Protein determinations were carried out in duplicate using 5 ul of homogenate according to the method of Smith et al (1985). Serotonin and its principle metabolite, 5-hydroxyindole-acetic acid (5-HIAA), were measured using an isocratic HPLC elution system and electrochemical detection, using a 16 channel coulometric array detector (ESA, Inc., Bedford, Mass.; Gamache et al, 1991 Neurosci. Abstracts 17:985.).

1.17 Statistical Analysis

The statistical significance of changes in rotational behavior, and neurochemical measurements were assessed with one-way analysis of variance followed by Dunnet's t and Neuman-Keuls post-hoc comparison tests (Winer, B. J. Statistical Principles in Experimental Design, McGraw-Hill, NY 1971.)

1.2 Results

1.21 Forced Swim Test

FIG. 1 demonstrates that BDNF infusion in the midbrain decreased the immobility time in the forced swim test as compared to vehicle-infused controls. The vehicle infused rats were immobile for 155.5+27.8 seconds of the 300 seconds comprising the 5 minute post-drug test. In contrast, the BDNF-infused rats remained immobile for an average of 46.6+16.8 seconds, representing a 70% decrease.

1.22 Changes in Locomotor Activity

Figure 2:
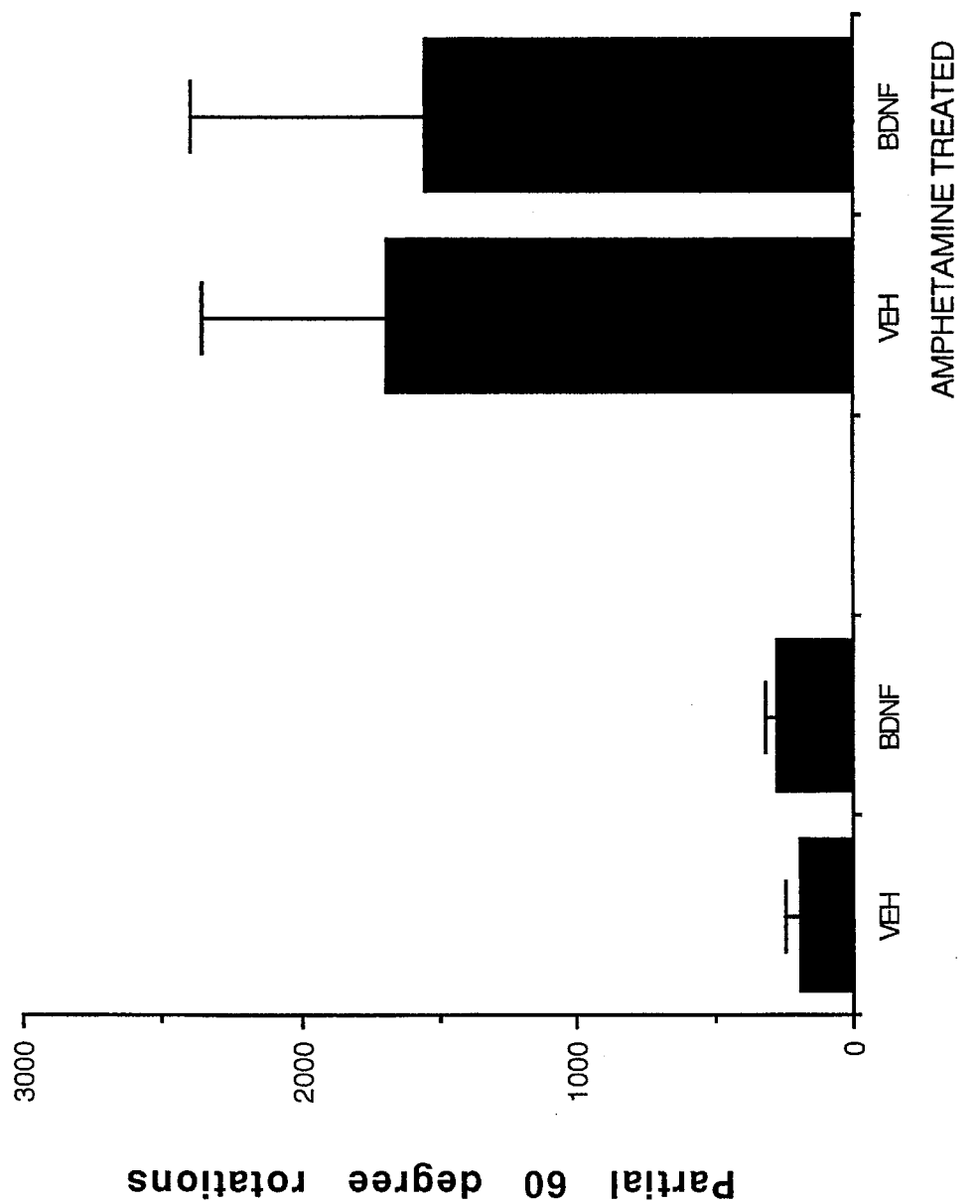
FIG. 2 Total 60° partial rotations in rats receiving midbrain infusions of PBS vehicle or BDNF (24 ug/day), with or without prior treatment of d-amphetamine (3.3 mg/kg; i.p.). Activity was measured for 80 minutes. The values shown are mean+SEM for 4–8 rats/group.

In order to demonstrate that general changes in locomotor activity could not account for the reduction of immobility time in the forced swim test, midbrain infused rats were also assessed for changes in locomotor activity. FIG. 2 demonstrates that BDNF infusion produced no changes in locomotor activity as measured by 60° partial rotation behavior either with or without prior d-amphetamine administration.

1.23 Changes in Serotonin Levels

Measurements of 5 HT and 5 HIAA levels in the hippocampus and nucleus accumbens of rats infused for 14 days with either phosphate buffered saline vehicle or BDNF are shown in Table 1. The 5HIAA/5HT ratio in the hippocampus (62% increase, t=3.8, df=13, p=0.0029) and nucleus accumbens (33% increase, t=2.5, df=13, p=0.029) were significantly elevated following 14 days of continuous midbrain infusion of BDNF indicating an increase in serotonergic activity. 5-HIAA levels were also elevated in the hippocampus (67% increase, t=3.9, df=13, p=0.002).

TABLE 1

5HT AND 5HIAA CONCENTRATIONS AND THE 5HIAA/5HT RATIO IN THE HIPPOCAMPUS AND NUCLEUS ACCUMBENS FOLLOWING MIDBRAIN INFUSION.

| TREATMENT | 5HT pg/ug protein | 5HIAA pg/ug protein | 5HIAA/5HT ratio |
|---|---|---|---|
| HIPPOCAMPUS | | | |
| VEHICLE-INFUSED | 2.6 + 0.2 (8) | 2.4 + 0.2 (8) | 0.98 + 0.07 (8) |
| BDNF-INFUSED | 2.6 + 0.3 (7) | 4.0 + 0.4 67%↑(7)* | 1.59 + 0.15 62%↑(7)* |
| NUCLEUS ACCUMBENS | | | |
| VEHICLE-INFUSED | 6.9 + 1.0 (8) | 7.9 + 0.9 (8) | 1.19 + 0.07 (8) |
| BDNF-INFUSED | 7.2 + 1.3 (7) | 10.8 + 1.9 (7) | 1.58 + 0.15 33%↑(7)* |

5HT and 5HIAA concentrations and the 5HIAA/5HT ratio in the hippocampus and nucleus accumbens of rats which received 14 days of continuous infusion of PBS vehicle or BDNF 12 ug/day in the midbrain near the periaqueductal gray and dorsal and median raphe nuclei. Values shown are mean ± sem. Number of animals is shown in parentheses.
*$p < 0.05$ vs. vehicle.

I claim:

1. A method for treating a mammal with depression comprising administering to the midbrain of said mammal a pharmaceutically effective dose to treat depression of at least one neurotrophin or peptide or fragment thereof selected from the group consisting of brain-derived neurotrophic factor, neurotrophin-3, and neurotrophin-4.

2. The method of claim 1, wherein the mammal is a human.

3. The method of claim 2 wherein said neurotrophin is human brain derived neurotrophic factor.

* * * * *